(12) United States Patent
Berz

(10) Patent No.: US 11,045,149 B2
(45) Date of Patent: *Jun. 29, 2021

(54) METHOD AND APPARATUS FOR MONITORING DEVELOPMENT OF MEDICATION INDUCED FEBRILE NEUTROPENIA

(71) Applicant: ALACRITY PATIENT SERVICES, INC., San Francisco, CA (US)

(72) Inventor: David Berz, Los Angeles, CA (US)

(73) Assignee: ALACRITY PATIENT SERVICES, INC., San Francisco, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/436,035

(22) Filed: Jun. 10, 2019

(65) Prior Publication Data
US 2019/0290213 A1 Sep. 26, 2019

Related U.S. Application Data

(63) Continuation of application No. 14/333,341, filed on Jul. 16, 2014, now Pat. No. 10,314,549.

(51) Int. Cl.
*A61B 5/00* (2006.01)
*A61B 5/0295* (2006.01)
(Continued)

(52) U.S. Cl.
CPC .......... *A61B 5/7282* (2013.01); *A61B 5/0022* (2013.01); *A61B 5/02028* (2013.01);
(Continued)

(58) Field of Classification Search
CPC . A61B 5/7282; A61B 5/02055; A61B 5/0295; A61B 5/02028; A61B 5/6802;
(Continued)

(56) References Cited

U.S. PATENT DOCUMENTS

| 4,246,344 A | 1/1981 | Silver, III | G01N 33/5094 |
| 5,025,791 A | 6/1991 | Niwa | A61B 5/14552 |

(Continued)

OTHER PUBLICATIONS

Children's Hospital of Orange County ("Febrile Neutropenia Oncology Care Guideline" 2011.
(Continued)

*Primary Examiner* — Nathan J Jenness
(74) *Attorney, Agent, or Firm* — Hayes Soloway P.C.

(57) ABSTRACT

Systems and methods for home monitoring and detection of febrile neutropenia in a patient are provided. The system includes a photoplethysmographic sensor for sensing photoplethysmographic signals of the patient, and one or more blood borne parameter sensors for sensing parameters in the patient's blood. A febrile neutropenia monitoring application receives information sensed by the photoplethysmography sensor and the one or more blood borne parameter sensors and determines, based on the received information, the presence or deterioration of febrile neutropenia. The method includes the steps of: sensing photoplethysmographic signals of the patient with a photoplethysmographic sensor worn by the patient; sensing blood borne parameters in the patient's blood with one or more blood borne parameter sensors; transmitting the sensed photoplethysmographic signals and blood borne parameters to a febrile neutropenia monitoring application; and determining, by the febrile neutropenia monitoring application, the presence or deterioration of febrile neutropenia based on the received information.

13 Claims, 3 Drawing Sheets

(51) Int. Cl.
*A61B 5/02* (2006.01)
*A61B 5/0205* (2006.01)
*A61B 5/145* (2006.01)

(52) U.S. Cl.
CPC .......... *A61B 5/0295* (2013.01); *A61B 5/4833* (2013.01); *A61B 5/746* (2013.01); *A61B 5/02055* (2013.01); *A61B 5/145* (2013.01); *A61B 5/6802* (2013.01); *A61B 5/7207* (2013.01)

(58) Field of Classification Search
CPC ....... A61B 5/145; A61B 5/746; A61B 5/7207; A61B 5/4833; A61B 5/0022
USPC .................................................. 600/300, 301
See application file for complete search history.

(56) References Cited

U.S. PATENT DOCUMENTS

| | | | |
|---|---|---|---|
| 5,967,975 A | 10/1999 | Ridgeway | G06F 19/3418 |
| 6,594,011 B1 | 7/2003 | Kempen | 356/369 |
| 6,859,280 B2 | 2/2005 | Kempen | 356/369 |
| 6,882,420 B2 | 4/2005 | Rassman et al. | 356/369 |
| 7,002,686 B2 | 2/2006 | Lieberman et al. | 356/369 |
| 7,023,547 B2 | 4/2006 | Venkatasubbarao et al. | 356/369 |
| 7,193,711 B2 | 3/2007 | Rassman et al. | 356/369 |
| 7,518,724 B2 | 4/2009 | Rassman et al. | 356/369 |
| 7,890,153 B2 | 2/2011 | Hoarau | A61B 5/062 |
| 8,039,270 B2 | 10/2011 | Dultz et al. | 436/518 |
| 8,355,133 B2 | 1/2013 | Dultz et al. | 356/445 |
| 2005/0209516 A1 | 9/2005 | Fraden | A61B 5/02055 |
| 2006/0085227 A1 | 4/2006 | Rosenfeld | G06F 19/322 |
| 2007/0043269 A1 | 2/2007 | Mannheimer | A61B 5/14551 |
| 2007/0273504 A1* | 11/2007 | Tran | A61B 5/02108 340/539.12 |

OTHER PUBLICATIONS

Penack et al. "Management of sepsis in neutropenic patients: guidelines from the infectious diseases working party of the German Society of Hematology and Oncology" Annals of Oncology vol. 22, Issue 5, May 1, 2011, pp. 1019-1029 (Published Nov. 1, 2010).

Povoa P, Souza-Dantas VC, Soares M, Salluh JF C-reative protein in critically ill cancer patients with sepsis: influence of neutropenia Crit Care. 2011;15(3):R129. doi: 10.1186/cc10242. Epub May 19, 2011.

Sakr, Y., Sponholz, C., Tuche, F. et al. The Role of Procalcitonin in Febrile Neutropenic Patients: Review of the Literature. Infection (2008) 36: 396. doi:10.1007/s15010-008-7374-y.

Uzun, O, Anaissie E. Outpatient therapy for febrile neutropenia: who, when and how? . Antimicrob. Chemother. (1999)43 (3): 317-320.doi: 10.1093/jac/43.3.317.

* cited by examiner

METHOD AND APPARATUS FOR MONITORING DEVELOPMENT OF MEDICATION INDUCED FEBRILE NEUTROPENIA

CROSS REFERENCE TO RELATED APPLICATIONS

This application is a continuation application of U.S. patent application Ser. No. 14/333,341, filed Jul. 16, 2014, now U.S. Pat. No. 10,314,549, issued Jun. 11, 2019, which in turn, claims priority from U.S. Provisional Application Ser. No. 61/846,980, filed Jul. 16, 2013, the contents of which are incorporated herein by reference.

FIELD OF THE INVENTION

The present disclosure is generally related to home monitoring of a patient's health, and more particularly is related to systems and methods home monitoring and detection of febrile neutropenia in a patient.

BACKGROUND OF THE INVENTION

The present invention relates to a system, i.e. method and apparatus for monitoring development of medication induced febrile neutropenia. The invention has particular utility in connection with the monitoring of chemotherapy induced febrile neutropenia, and will be described in connection with such utility, although other utilities are contemplated.

Immune dysregulation is a component of many pathological diseases or conditions. Such dysregulation may be a factor that favors the establishment, maintenance or progression of diseases or conditions. Immune response or immune suppression also frequently results from medication treatments including specifically chemotherapy that is used in the treatment of cancer.

Outpatient therapy for low-risk neutropenic patients is considered safe, but remains an uncommon practice. However, even with regular monitoring, including frequent in-office or outpatient monitoring, patients frequently get into trouble resulting in costly hospitalizations for treatment of chemotheraphy induced febrile neutropenia, since by the time the patient is diagnosed, it often is too late for treatment other than through administration of paranteral antibiotics.

Although the definition for chemotherapy induced febrile neutropenia vary across institutions and guidelines, most North American Societies define a single oral temperature of >38.3° C. (101.3° F.) or a temperature of >38° C. (100.4° F.) sustained for >1 hour as significant and neutropenia with an ANC<1000 cells/microL, whilst severe neutropenia is considered an absolute neutrophil count (ANC)<500 cells/microL, or an ANC that is expected to decrease to <500 cells/microL over the next 48 hours[1]. In spite of the wide utilization of growth factors and prophylactic antimicrobial therapy in patients obtaining chemotherapy for their malignant disease, febrile neutropenia still remains a common treatment related complication[2]. Early studies linked infections in the context of severe neutropenia with a substantial mortality rate[3].

The corresponding concern of the development of an overwhelming sepsis episode rendered hospitalization with the administration of parenteral antibiotics as the standard of care in the management of patients with febrile neutropenia for many decades. It is now well recognized that neutropenic fever patients represent a very heterogeneous group[4]. The Multinational Association for the Supportive Care in Cancer (MASCC) proposed a seven point model, consisting of (1) degree of symptom burden, (2) presence or absence of hypotension, (3) need for IV fluid resuscitation, (4) presence or absence of COPD as a comorbidity, (5) solid tumor malignancy or hematologic malignancy without prior fungal infection, (6) outpatient status and (7) age above or below sixty years old as relevant clinico-demographic cofactors for the risk stratification of patients presenting with chemotherapy induced febrile neutropenia[4]. At least seven randomized trials have established the use of outpatient antibiotics as a safe and efficacious strategy in low risk febrile neutropenia[5-11]. In addition, the comparability of oral with intravenous regimens has been demonstrated[12-15]. Several guidelines support the use of outpatient antibiotics in the low risk settingl[16-18]. A recent systematic review with meta-analysis revealed equal mortality with inpatient versus outpatient therapy with comparables rates of treatment failure[2]. Benefits of outpatient therapy in this setting include increased patient acceptance and the absence of exposure to a nosocomial environment. In addition, recent health economic comparisons of inpatient versus outpatient therapy in the low risk neutropenic feversetting have demonstrated striking savings with outpatient therapy[19,20].

In spite of the available feasibility data and the benefits of outpatient therapy vs inpatient therapy described above, a large amount of patients with chemotherapy associated neutropenic fever are still admitted to the hospital for parenteral IV antibiotic therapy for the full length of their neutropenic presentation. A major reason for this is concern of further deterioration following the initial assessment at presentation.

SUMMARY OF THE INVENTION

The present invention provides a remote monitoring solution which permits early detection of chemotherapy associated febrile neutropenia, and which often permits patients to be safely cared for in their own home environment, i.e. by early administration of oral antibiotics. An integrated algorithm captures early signs of deterioration, which might otherwise lead to hospitalization of the patient, and alerts the patient and medical personnel to begin administration or oral antibiotics before clinical characteristics render the patient a high-risk patient requiring hospitalization.

The multinational association for the supportive care in cancer patients (MASCC) proposes a weighted seven variable algorithm for the clinic-demographic assessment of a patient with chemotherapy related neutropenic fever[4]:

(1) degree of symptom burden
(2) presence or absence of hypotension
(3) need for IV fluid resuscitation
(4) presence or absence of COPD as a comorbidity
(5) solid tumor malignancy or hematologic malignancy without prior fungal infection
(6) outpatient status
(7) age, i.e. above or below sixty years old However, other, in certain aspects simpler algorithms have been proposed. The Infectious Diseases Society of America (IDSA) has proposed a ten point algorithm to stratify a patient with chemotherapy related febrile neutropenia as high or low risk. Any of the following clinical characteristics renders the patient as a high-risk patient.

1. ANC≤100 cells/microL expected to last >7 days
2. Hemodynamic instability
3. Oral or gastrointestinal tract mucositis limiting swallowing or causing severe diarrhea 4. Gastrointestinal symptoms, such as abdominal pain, nausea and vomiting, or diarrhea
5. Neurologic or mental status changes of new onset
6. Intravascular catheter infection
7. New pulmonary infiltrate or hypoxia
8. Underlying chronic lung disease
9. Evidence of hepatic insufficiency (defined as aminotransferase levels >5 times normal values)
10. renal insufficiency (defined as a creatinine clearance <30 mL/min In addition, the National Comprehensive Cancer Network (NCCN) proposes a more detailed breakdown of patients with chemotherapy related febrile neutropenia as high, intermediate or low risk[21].

In addition to including an intermediate risk strata, the NCCN also includes the exposure to certain heavily immune-compromising anti-neoplastic agents (such as alemtuzumab) as risk factors.

High-risk—The NCCN categorizes febrile neutropenic patients as high-risk if any of the following criteria are met:
Inpatient status at time of development of fever
Significant medical comorbidity or presence of clinical instability
Anticipated prolonged profound neutropenia (ANC≤100 cells/microL expected to last >7 days)
Hepatic insufficiency (defined as aminotransferase levels >5 times normal values) or renal insufficiency (defined as a creatinine clearance <30 mL/min)
Uncontrolled progressive cancer defined as any leukemic patient not in complete remission, or any non-leukemic patient with evidence of disease progression after more than two courses of chemotherapy
Pneumonia or other complex infection at clinical presentation
Alemtuzumab exposure within the past two months
Grade 3 or 4 mucositis
Multinational Association for Supportive Care in Cancer (MAS CC) risk index score
<21

Intermediate risk—In addition to the categories of high-risk and low-risk described above, the NCCN defines febrile neutropenic patients to be intermediate-risk for complications if any of the following criteria are met:
Autologous HCT
Lymphoma
Chronic lymphocytic leukemia
Multiple myeloma
Purine analog therapy
Anticipated duration of neutropenia of 7 to 10 days Low-risk—The NCCN categorizes febrile neutropenic patients as low-risk for complications if they do not meet any of the high-risk criteria described above and if they meet most of the following criteria:
Outpatient status at time of development of fever
No associated acute comorbid illness requiring inpatient hospitalization or close observation
Anticipated short duration of severe neutropenia (ANC≤100 cells/microL expected to last 7 days or fewer)
Good performance status (Eastern Cooperative Oncology Group ~ECOG1 0-1
No hepatic insufficiency
No renal insufficiency
Multinational Association for Supportive Care in Cancer (MASCC) risk index score
≥21

The present invention provides a system involving both hardware and software tools for monitoring and measuring a patient's health, and for assessing a change in a patient's condition, changing his/her risk status and the corresponding clinical approach.

Embodiments of the present disclosure provide systems and methods for home monitoring and detection of febrile neutropenia in a patient. Briefly described, in architecture, one embodiment of a system, among others, can be implemented as follows. The system includes a wearable photoplethysmographic sensor for sensing photoplethysmographic signals of the patient, and one or more blood borne parameter sensors for sensing parameters in the patient's blood. A febrile neutropenia monitoring application is hosted at least partially on a server and electronically accessible over at least one network system to a patient computer. The febrile neutropenia monitoring application is configured to receive information sensed by the photoplethysmography sensor and the one or more blood borne parameter sensors and to determine, based on the received information, the presence or deterioration of febrile neutropenia.

In one embodiment, the system further comprises a wearable movement sensor for sensing movement of the patient, wherein the photoplethysmographic signals are corrected based on information sensed by the movement sensor, In another embedment, the system further comprises a healthcare provider computer, wherein the febrile neutropenia monitoring application is further configured to provide an alarm to the healthcare provider computer upon a determination of the presence or deterioration of febrile neutropenia in the patient.

In one embodiment, the febrile neutropenia monitoring application is further configured to provide an alarm to the healthcare provider computer upon a determination of patient non-compliance with a patient monitoring protocol.

In yet another embodiment the system further comprises a temperature sensor for sensing the patient's body temperature, wherein the febrile neutropenia monitoring application is further configured to receive information sensed by the temperature sensor and to determine the presence or deterioration of febrile neutropenia based at least in part on the sensed temperature information.

In still yet another embodiment, the system further comprises at least one of a blood pressure sensor and a scale for measuring the patient's weight, wherein the febrile neutropenia monitoring application is configured to receive information sensed by the at least one of a blood pressure sensor and scale and to determine the presence or deterioration of febrile neutropenia based at least in part on the information sensed by the at least one of a blood pressure sensor and scale.

In one embodiment the febrile neutropenia monitoring application is further configured to determine the patient's peripheral vascular resistance and heart rate based on the information sensed by the photoplethysmographic sensor.

In yet another embodiment the blood borne parameter sensors comprise a cell-based assay for sensing or counting at least one of neutrophils and monocytes.

In still yet another embodiment the blood borne parameter sensors comprise a multiplex biochemical assay for detecting at least one of: interleukin 1 and 6; tumor necrosis factor; procalcitonin; and C-reactive protein.

In yet another embodiment the febrile neutropenia monitoring application is further configured to provide a communication to the patient computer, upon a determination of the presence or deterioration of febrile neutropenia in the patient, said communication prompting the patient to perform at least one of: seeking professional medical care, and begin taking antibiotics.

In another embodiment, a method for home monitoring and detection of febrile neutropenia in a patient is provided that includes the steps of: sensing photoplethysmographic signals of the patient with a photoplethysmographic sensor worn by the patient; sensing blood borne parameters in the patient's blood with one or more blood borne parameter sensors; transmitting the sensed photoplethysmographic signals and blood borne parameters to a febrile neutropenia monitoring application; and determining, by the febrile neutropenia monitoring application, the presence or deterioration of febrile neutropenia based on the received information.

In one embodiment the method further comprises sensing movement of the patient with a wearable movement sensor; and correcting the photoplethysmographic signals based on information sensed by the movement sensor.

In another embodiment, the method comprises providing, by the febrile neutropenia monitoring application, an alarm to a healthcare provider computer upon a determination of the presence or deterioration of febrile neutropenia in the patient.

In yet another embodiment, the method further comprises providing, by the febrile neutropenia monitoring application, an alarm to a healthcare provider computer upon a determination of patient non-compliance with a patient monitoring protocol.

In still yet another embodiment, the method further comprises sensing the patient's body temperature with a temperature sensor, wherein the determining, by the febrile neutropenia monitoring application, of the presence or deterioration of febrile neutropenia is further based on the sensed temperature information.

In another embodiment, the method comprises sensing at least one of the patient's blood pressure and weight, wherein the determining, by the febrile neutropenia monitoring application, is further based on the at least one of a blood pressure and weight information.

In yet another embodiment, the method comprises determining, by the febrile neutropenia monitoring application, determine the patient's peripheral vascular resistance and heart rate based on the information sensed by the photoplethysmographic sensor.

In still yet another embodiment, the blood borne parameter sensors comprise a cell-based assay for sensing or counting at least one of neutrophils and monocytes.

In yet another embodiment, the blood borne parameter sensors comprise a multiplex biochemical assay for detecting at least one of: interleukin 1 and 6; tumor necrosis factor; procalcitonin; and C-reactive protein.

Yet another embodiment comprises providing, by the febrile neutropenia monitoring application, a communication to a patient computer, upon a determination of the presence or deterioration of febrile neutropenia in the patient, said communication prompting the patient to perform at least one of: seeking professional medical care, and begin taking antibiotics.

In yet another embodiment, a non-transitory computer readable medium is provided that contains instructions for home monitoring and detection of febrile neutropenia in a patient enabled at least in part on a processor of a computerized device, the instructions, which when executed by the processor, performing the steps of: receiving photoplethysmographic signals of the patient from a photoplethysmographic sensor worn by the patient; receiving blood borne parameters in the patient's blood from one or more blood borne parameter sensors; and determining the presence or deterioration of febrile neutropenia based on the information received from the photoplethysmographic sensor and the one or more blood borne parameter sensors.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE PRESENT INVENTION

Figure 1:
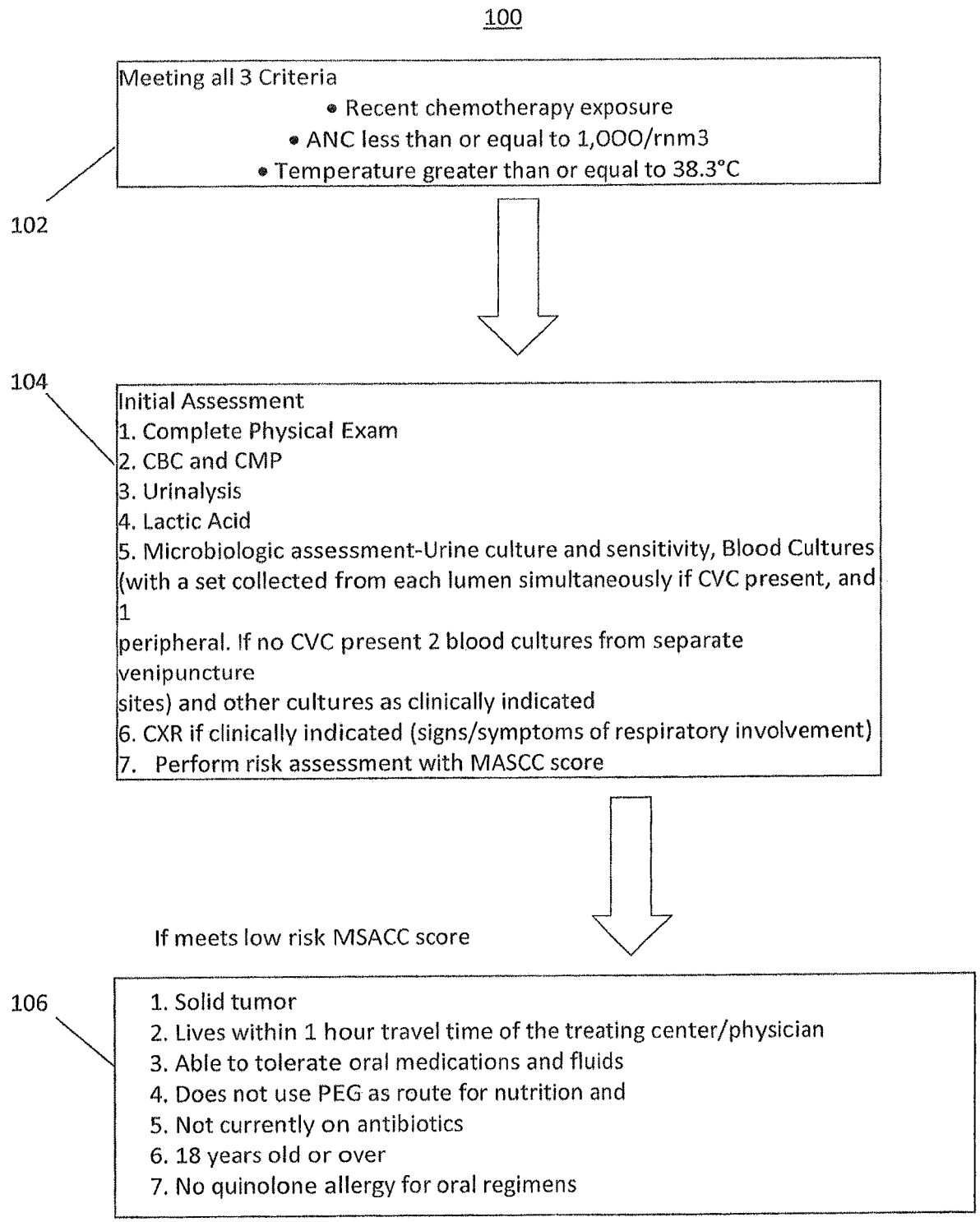
FIG. 1 is a flow chart which schematically illustrates methods for evaluating whether a patient is suited for home monitoring for febrile neutropenia, in accordance with embodiments of the present disclosure.

The present invention employs peripheral point-of-care devices, such as described herein, which allow for home monitoring of certain patient's vital statistics, combined with computer-executable instructions, including algorithms executed by a programmable computer.

Many embodiments of the present invention may take the form of computer-executable instructions, including algorithms executed by a programmable computer. However, the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The invention also can be practiced in distributed computing environments, where tasks or modules are performed by remote processing devices that are linked through a communications network. Moreover, the invention can be practiced in Internet-bases or cloud computing environments, where shared resources, software and information may be provided to computers and other devices on demand. In a distributed computing environment, program modules or subroutines may be located in both local and remote memory storage devices. Aspects of the disclosure described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the disclosure are also encompassed within the scope of the invention.

Neutropenic fever is defined by a physiology underlying the systemic inflammatory response syndrome (SIRS)[22] and sepsis. Hence, deterioration is clinically indicated by a deterioration of the physiologic parameters defining the SIRS, i.e. along with the cell count parameters (neutrophil/monocyte count) also the pulse rate, respiration rate and temperature. Further deterioration is then indicated by evidence of hypo-perfusion and organ dysfunction[22,23]. This is evidenced by blood pressure drop, decrease in cardiac output, change in peripheral vascular resistance and occasionally disseminated intravascular coagulation as well as mental status deterioration and decreased renal function.

Many, if not all, of the hallmarks of the SIRS and most clinical signs of early deterioration are accessible by currently available peripheral point of care devices (PPCD).

In some embodiments provided herein, parameters assessed include:
Blood count
Body temperature
Pulse rate
Capillary C02 tension
Blood pressure/Systemic Vascular Resistance These physiologic parameters can be periodically or continuously measured on patients with neutropenic fevers. An integrated, unique algorithm signals early deterioration which ideally can be treated in the patient's home or the doctor's office before the deterioration becomes so severe as to lead to hospitalization.

FIG. 1 is a flowchart 100 illustrating methods for evaluating whether a patient is suited for home monitoring for medication induced febrile neutropenia, in accordance with an exemplary embodiment of the present disclosure. As shown at block 102, satisfaction of three initial criteria may be required before a further, initial assessment is performed on the patient. At block 104, an initial assessment is performed, which includes various assessments and/or analysis, including: a complete physical exam; CBS and CMP; urinalysis; lactic acid; microbiologic assessment; CXR if clinically indicated; and a risk assessment with MASCC score.

If results from the initial assessment indicate that the patient meets a low-risk MSACC score, further criteria may require satisfaction before deeming the patient suitable for remote home monitoring, as shown at block 106. Such criteria may include: the presence of a solid tumor; the patient lives within 1 hour (or some other suitable time/distance) of the treating center/physician; ability to tolerate oral medications and fluids; does not use PEG as route for nutrition; not currently on antibiotics; at least 18 years of age; and no quinolone allergy for oral regimens.

Figure 2:
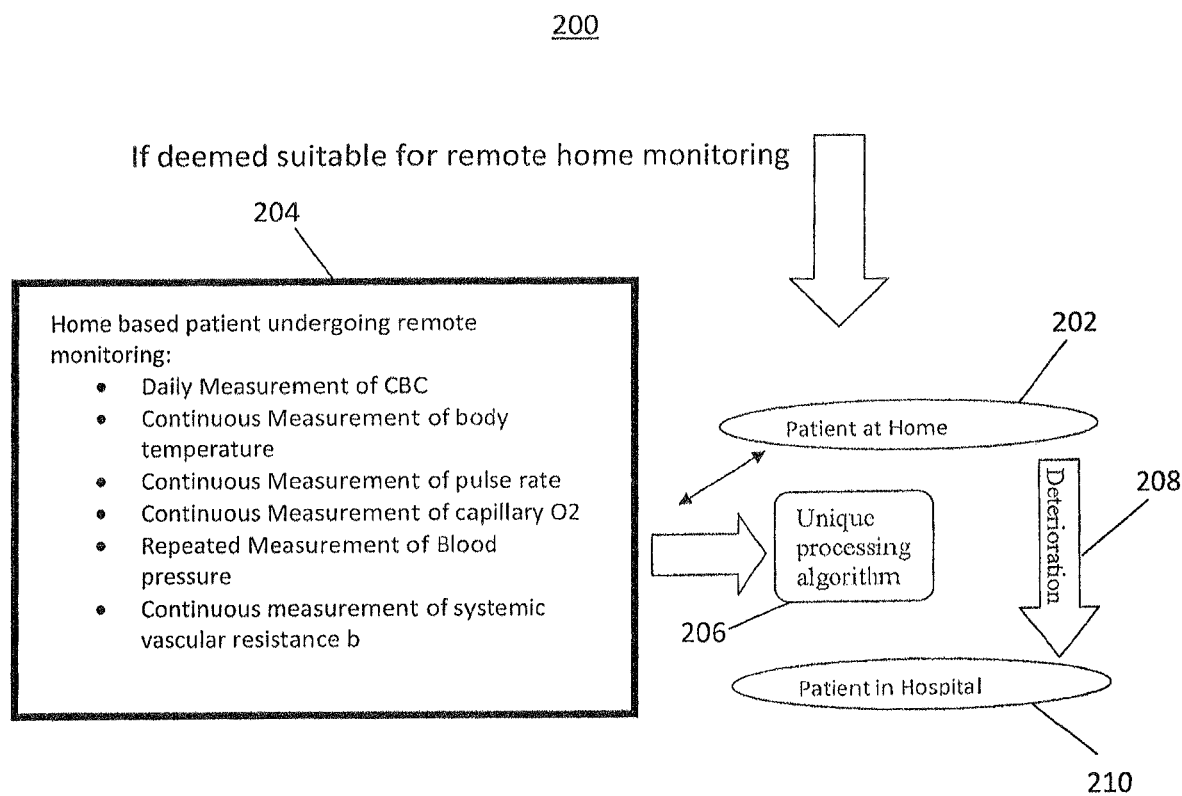
FIG. 2 is a flow chart which schematically illustrates a method for home monitoring and detection of febrile neutropenia in a patient, in accordance with embodiments of the present disclosure.

If it is determined that a patient is well-suited for home monitoring, e.g., after satisfaction of the evaluation as shown in FIG. 1, the patient may begin home monitoring for medication induced febrile neutropenia, as shown in FIG. 2. FIG. 2 is a flowchart 200 illustrating a method for home monitoring of a patient for medication induced febrile neutropenia, in accordance with embodiments provided by this disclosure.

As shown at 202, a patient's health parameters are monitored using one or more point-of-care monitoring devices. As shown at 204, monitored health parameters may include, for example: a daily measurement of complete blood count (CBC); continuous measurement of body temperature; continuous measurement of pulse rate; continuous measurement of capillary $O_2$; repeated measurement of blood pressure; and continuous measurement of systemic vascular resistance.

Various peripheral point-of-care devices exist for home monitoring of health parameters of a patient, and may be included in the systems and methods provided herein for home monitoring of a patient for medication induced febrile neutropenia. These include blood pressure monitors available from A & D and other vendors, blood glucose monitors available from MyClinicalHealth, Lifescan J & J and other vendors, thermometers available from Cardi Scientific and other vendors, pulse oximeters (pulse ox meters) available from Nonin and other vendors, peak flow monitors available from Microlife and other vendors, pedometers available from Omron and other vendors, and weight scales available from A & D Medical and other vendors. Many of these devices have been around for years. More recently point-of-care cell analyzers have been developed for blood cell counting and moving from the laboratory to home use. See "Integrated Systems for Rapid Point of Care (POC) Blood Cell Analysis" by vanBarkel et al, The Royal Society of Chemistry 2010, the entirety of which is incorporated herein by reference.

Many of the currently available monitors are fully automated and require no patient intervention. Others require simple prompting by the patient. Mass production of these monitors also has brought the cost of such monitors down significantly. Several commercially available monitors include communication capabilities also for communicating with the computer either through hard wiring, or wirelessly. As the cost of computers also continues to fall, there presents an opportunity to reduce patient risks and costs, and at the same time improve patient outcome.

The health monitoring devices may be worn by the patient continuously while in an outpatient setting, such as at the patient's home, thereby providing continuous monitoring of the various health parameters. Alternatively, the patient may be prompted, e.g. by a timer or the like to periodically don the monitors for a reading. In order to ensure patient compliance, in an embodiment, one or more of the monitors may communicate, for example, wirelessly, to a central computer which would alert health care personnel if the patient fails to timely present his or herself for monitoring.

Information sensed by the healthcare monitoring devices may be processed by an algorithm, at 206, to determine a state of the patient's health, such as the presence of, or risk of developing, febrile neutropenia. The healthcare monitoring devices and/or a computer system running the algorithm may then provide an alert to health care personnel if the parameters assessed by the devices indicate clinical signs of early deterioration of the patient's health, at 208. Where early clinical signs of patient health deterioration are determined, the patient may be prompted to seek professional medical care (e.g., such as admission to a hospital, at 210) or to begin taking oral antibiotics which could be supplied to the patient ahead of time, or supplied, e.g. by a pharmacy, which may also be prompted by the system to dispense a course of antibiotics. Also, again to ensure patient compliance, the health care professional may be advised of a patient's health deterioration so that the health care professional could contact the patient if the patient does not make the contact first.

Figure 3:
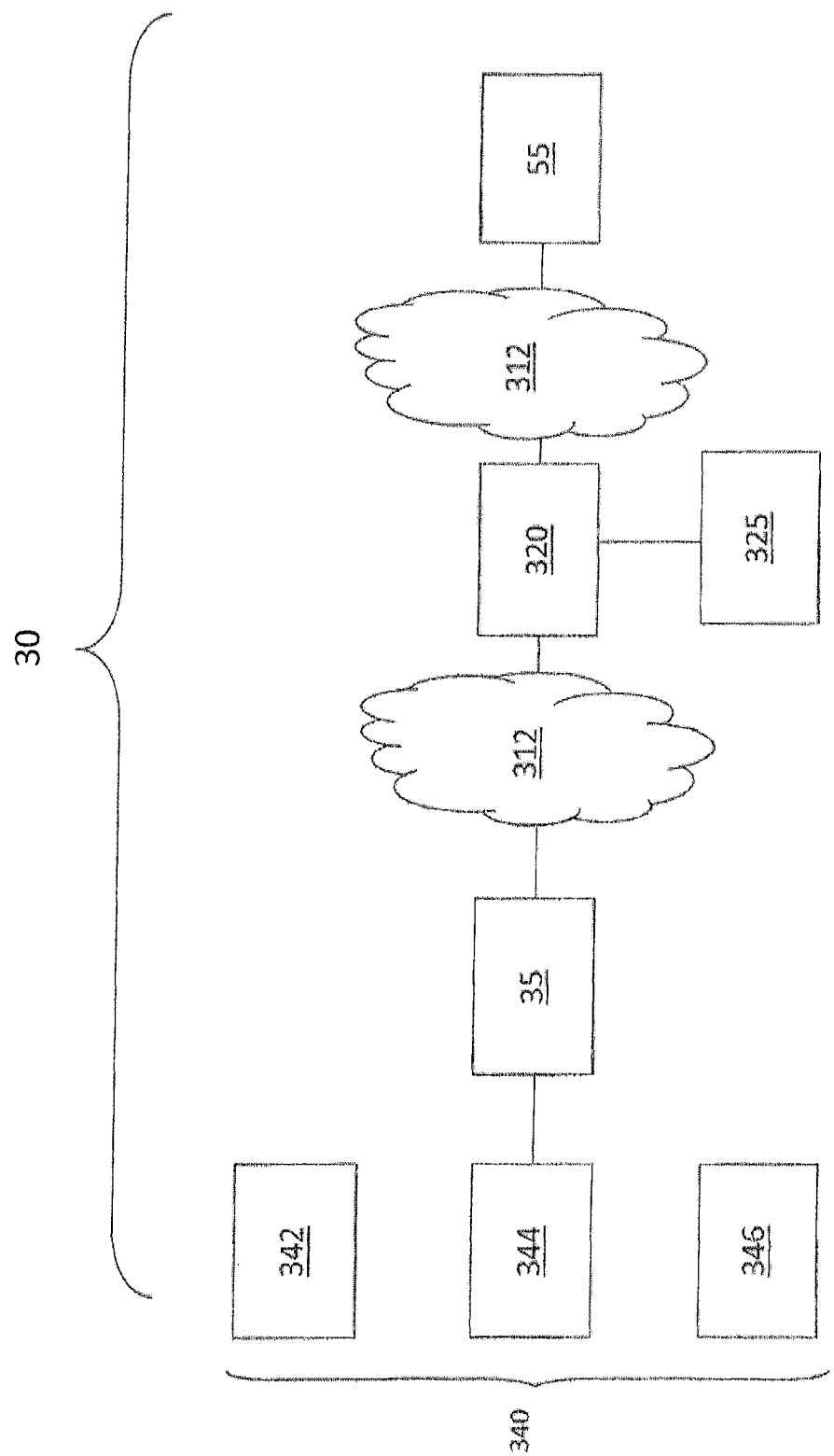
FIG. 3 is a schematic illustration of a system for home monitoring and detection of febrile neutropenia, in accordance with embodiments of the disclosure.

FIG. 3 is a schematic illustration of a system for home monitoring and detection of febrile neutropenia 30, in accordance with an exemplary embodiment of the present disclosure. The system for home monitoring and detection of febrile neutropenia 30, which may also be referred to as 'system 30', includes a febrile neutropenia monitoring application 325, which may be electronically accessible over at least one network system 312 and hosted at least partially on a server 320. A patient computer 35 is positioned to access the application 325, and a healthcare provider computer 55 may further be positioned to access the application 325. The system 30 further includes a variety of patient monitoring devices 340, which may include a photoplethysmographic sensor 342, movement sensor 344 and one or more blood borne parameter sensors 346.

The server 320 may be or include any database capable of storing and/or providing access to information, such as an electronic database, a computer and/or computerized server, database server or generally any network host capable of storing data and connected to any type of data network. Further, the server 320 may include or be a part of a distributed network or cloud computing environment. Any type of electronic and/or computerized device that is capable of storing information may be included as the server 320, and is considered within the scope of this disclosure. The server 320 may include computer-readable storage media, and a processor for processing data and executing algorithms, including any of the processes and algorithms set forth in this disclosure. The febrile neutropenia monitoring application 325 is electronically accessible over at least one network system 312. The network system 312 may include any type of network infrastructure, such as the Internet, or any other wired, wireless and/or partially wired network. The server 320, application 325 and network system 312 may include a variety of hardware and software components to provide successful functioning of the server 320 and the application 325, as is well-known within the art. Further, any features, characteristics, designs and/or functions that are known within the art may be included with the system 30 to further enhance its efficiency.

The patient computer 35 may be any computerized device that is capable of communicating with the application 325, for example via a network system 312, and may be operated by any patient for home monitoring of febrile neutropenia, or any representative thereof. Similarly, the healthcare provider computer 55 may be any computerized device that is capable of communicating with the application 325, for example via a network system 312, and may be operated by any physician, nurse or other healthcare provider, or any representative thereof. Any number of patient computers 35 and healthcare provider computers 55 may use the system 30 at any given time. The patient computer 35 and healthcare provider computer 55 may access the application 325 through a variety of ways, including through a computerized device in communication with the system 30 over a network system. For example, the patient computer 35 and/or healthcare provider computer 55 may be any computer, including any personal computer, Internet appliance, hand-held device (including palm-top computers, wearable computers, cellular or mobile phones, ipads, multi-processor systems, processor-based or programmable consumer electronics, network computers, minicomputers) and the like. One or more input devices, such as a keyboard or mouse, may be used to transmit information to and/or request information from the application 325 by the patient computer 35 and/or the healthcare provider computer 55.

The system 30 includes a plurality of point-of-care devices for monitoring or sensing parameters related to a patient's health (e.g., patient monitoring devices 340), which may be wearable monitoring devices that are operationally worn on the patient for measuring selected parameters as described herein. Readings from the patient monitoring devices 340 are transmitted to a computer (e.g., patient computer 35 and/or server 320) which includes or accesses the febrile neutropenia monitoring application 325 for monitoring and evaluating changes in the patient's vital statistics. The information sensed by the patient monitoring devices 340 may be transmitted directly to the server 320, or may be transmitted to the patient computer 35 (e.g., a patient's home-based computer, such as a laptop, desktop computer, smartphone or the like) which then communicates the sensed information to the application 325.

The febrile neutropenia monitoring application 325 may be fully or partially hosted on the server 320. Alternatively, the application 325 may be hosted and/or accessed on a patient's local computer, such as patient computer 35. The febrile neutropenia monitoring application 325 may include any tool, device, system, process or combination thereof, which assists or makes possible determining when a patient's measured parameters are approaching or are out of compliance with pre-determined criteria suggesting the onset or presence of febrile neutropenia, or deterioration of health in a patient with febrile neutropenia. The application 325 may include any computer-readable memory or databases, which may be stored in any computer-readable medium, and may be accessible by a computer processor. The application 325 may further include or access computer program instructions which may cause a processor to perform any algorithms and/or functions which may be described in this disclosure.

Further, the application 325 may provide access to a web or network-based platform, including a graphical user interface or webpage which provides interactive access to the system 30 to a user of a patient computer 35 and/or a healthcare provider computer 55. Alternatively or additionally, a patient computer 35 and/or healthcare provider computer 55 may include software providing access to the system 30.

The photoplethysmographic sensor 342 may be, for example, a wearable pulse oximeter. A wearable movement sensor 344 may be included to correct motion and/or gravitational interferences in the patient's photoplethysmographic signal. The patient's peripheral vascular resistance and the change in the peripheral vascular resistance may be determined from information sensed by the photoplethysmographic sensor 342. The patient's heart rate, an important vital parameter for the detection of febrile neutropenia and deterioration in febrile neutropenia, may be provided and/or determined (e.g., by the application 325) from the frequency of the photoplethysmographic signal. The patient's temperature may be recorded by a temperature sensor and transmitted to the application 325, as temperature may serve as a factor for the detection of febrile neutropenia and deterioration in febrile neutropenia. The patient monitoring devices 340 may further include a blood pressure sensor, such as a blood pressure cuff, and a scale for measuring the patient's weight. Additional patient monitoring devices 340 may be included for monitoring any health-related parameter which may be relevant to the determination of febrile neutropenia or deterioration of febrile neutropenia, including, for example, devices for monitoring or sensing any of the parameters listed at block 204 of FIG. 2.

Physiological parameters (e.g., as sensed by the photoplethysmographic sensor 342) may be correlated in real-time with blood borne parameters, such as sensed by blood borne parameter sensors 346. The blood borne parameter sensors 346 may include or utilize LFIRE (Label-Free Internal Reflection Ellipsometry) by Maven Technologies, LLC, as disclosed at least in part in one or more of the following U.S. patent Nos., each of which are incorporated in their entireties herein by reference: U.S. Pat. Nos. 6,594,011; 7,023,547; 6,859,280; 6,882,420; 7,002,686; 7,193,711; 7,518,724; 8,039,270; and 8,355,133.

The blood borne parameter sensors 346 may include cell-based assays for sensing or counting neutrophils and/or monocytes in a sample of the patient's blood, and may further include sensors for multiplex biochemical assays for simultaneous detection of binding events to nucleic acid or protein microarray on the sensor surface. Such multiplex biochemical assays may detect parameters relevant to a determination of febrile neutropenia or deterioration of febrile neutropenia such as: interleukin 1 and 6; tumor necrosis factor; procalcitonin; and C-reactive protein.

When neutropenia is suggested, the system 30 may raise an alarm prompting the patient or patient's caregiver to administer oral antibiotics and/or prompting the patient to seek medical care. For example, the application 325, upon determining that the information sensed by the patient monitoring devices 340 indicates the presence or deterioration of febrile neutropenia, may initiate an alarm or other communication to be transmitted to a healthcare provider computer 55.

By sensing and recording changes in a patient's selected parameters, early intervention, e.g. through administration of oral antibiotics may be prescribed. As a result, hospitalization of the patient may be avoided.

In a survey study, which was initially presented at the yearly ASCO meeting in 2004, 82% of physicians have claimed to treat some or all of their low-risk febrile neutropenic patients as outpatients while 17% exclusively used inpatient treatment[24]. Despite existing guidelines, 18 only one third of the responding physicians complied with the evidence based pattern of care[24]. Similar observation has been reported from studies in Canada and the UK, with the lowest acceptance towards outpatient treatment in low risk patients being observed in Europe[25,26].

Elting presented a retrospective analysis of 712 patients[27], who were prospectively treated on the University of Texas MD Anderson Cancer Center low-risk neutropenic fever algorithmpathway[15,28]. The patients, who were treated as outpatients were compared to a small subset of patients who were on clinical assessment candidates for the outpatient pathway, but were deemed on the grounds of psychosocial criteria, such as absence of access to caregivers at home, no telephone or no transportation in case of emergency or a history of non-compliance with other outpatient regimens not to be eligible for treatment as outpatients. Treatment as outpatient was in average associated with savings of 7.432$ in costs per neutropenic fever episode (15.231,$ vs 7.799$)[27].

Hendricks[19] evaluated the differences in costs between the in- and out-patient population in Talcott's randomized controlled trial[11]. This analysis included all financial aspects incurred by a patient with acute febrile neutropenic fever episode, including along with billing information from hospitals, outpatient clinicians and home care providers also indirect costs such as informal caregivers' time expense (family labor)[19]. Again, a striking difference between charges for the hospital vs home based care were observed with 15.495$ vs 7.868$. Even including indirect costs, such as opportunity costs for family members, the difference still remained highly significant 16.341$ vs 10.977$ (P<0.01), with basically identical clinical complication rates.

Teuffel's cost effectiveness analysis in the context of the Canadian health system[20] compared four different approaches, entire in hospital management with IV antibiotics until neutrophil recovery (HospIV), early discharge after a limited course of in hospital IV antibiotics, followed by home P0 antibiotics (EarlyDC), entire outpatient management with IV antibiotics (HomeIV) and entire outpatient management with P0 antibiotics (HomePO). The mean costs for the different approaches were 13.557C$, 6.15 C$, 4.83C$ and 3.470C$, reflecting a significant cost savings in each of the outpatient based treatment paradigms. The corresponding probabilistic willingness-to-pay analysis, which used a Canadian standard of 4.000C$ for quality of life adjusted febrile neutropenia episode, revealed cost effective results in 1% HospIV, 8% EarlyDC 38% HomeIV and 54% HomePO of all simulated outcomes, respectively[20].

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention.

All such modifications and variations are intended to be included herein within the scope of this invention and the present invention and protected by the following claims.

REFERENCES

Each of the following references are incorporated in their entireties herein, by reference:

1. Freifeld, A. G. et al. Clinical practice guideline for the use of antimicrobial agents in neutropenic patients with cancer: 2010 update by the infectious diseases society of America. *Clinical infectious diseases: an official publication of the Infectious Diseases Society of America* 52, e56-93 (2011).
2. Teuffel, O., Ethier, M C., Alibhai, S. M. H., Beyene, J. & Sung, L. Outpatient management of cancer patients with febrile neutropenia: a systematic review and meta-analysis. *Annals of oncology: official journal of the European Society for Medical Oncology/ESAJO* 22, 2358-65 (2011).
3. Bodey, G. P., Buckley, M., Sathe, Y. S. & Freireich, E. J. Quantitative relationships between circulating leukocytes and infection in patients with acute leukemia. *Annals of internal medicine* 64, 328-40 (1966).
4. Klastersky, J. et al. The Multinational Association for Supportive Care in Cancer risk index: A multinational scoring system for identifying low-risk febrile neutropenic cancer patients. *Journal of clinical oncology: official journal of the American Society of Clinical Oncology* 18, 3038-51 (2000).
5. Hidalgo, M. et al. Outpatient therapy with oral ofloxacin for patients with low risk neutropenia and fever: a prospective, randomized clinical trial. *Cancer* 85, 2 13-9 (1999).
6. Malik, I. A., Khan, W. A., Karim, M., Aziz, Z. & Khan, M. A. Feasibility of outpatient management of fever in cancer patients with low-risk neutropenia: results of a prospective randomized trial. *The American journal of medicine* 98, 224-31 (1995).
7. Rapoport, B. L. et al. Ceftriaxone plus once daily aminoglycoside with filgrastim for treatment of febrile neutropenia: early hospital discharge vs. Standard In-patient care. *Chemotherapy* 45, 466-76
8. Innes, H. E. et al. Oral antibiotics with early hospital discharge compared with inpatient intravenous antibiotics for low-risk febrile neutropenia in patients with cancer: a prospective randomised controlled single centre study. *British journal of cancer* 89, 43-9 (2003).
9. Santolaya, M. E. et al. Early hospital discharge followed by outpatient management versus continued hospitalization of children with cancer, fever, and neutropenia at low risk for invasive bacterial infection. *Journal of clinical oncology: official journal of the American Society of Clinical Oncology* 22, 3784-9 (2004).
10. Ahmed, N. et al. Early hospital discharge versus continued hospitalization in febrile pediatric cancer patients with prolonged neutropenia: A randomized, prospective study. *Pediatric blood & cancer* 49, 786-92 (2007).
11. Talcott, J. A. et al. Safety of early discharge for low-risk patients with febrile neutropenia: a multicenter randomized controlled trial. *Journal of clinical oncology: official journal of the American Society of Clinical Oncology* 29, 3 977-83 (2011).
12. Gupta, A., Swaroop, C., Agarwala, S., Pandey, R. M. & Bakhshi, S. Randomized controlled trial comparing oral amoxicillin-clavulanate and ofloxacin with intravenous ceftriaxone and amikacin as outpatient therapy in pediatric low-risk febrile neutropenia. *Journal of pediatric hematology/oncology* 31, 635-41(2009).
13. Minotti, V. et al. Domiciliary treatment of febrile episodes in cancer patients: a prospective randomized trial comparing oral versus parenteral empirical antibiotic treatment. *Supportive care in cancer: official journal of the Multinational Association of Supportive Care in Cancer* 7,134-9 (1999).
14. Sebban, C. et al. Oral moxifloxacin or intravenous ceftriaxone for the treatment of low-risk neutropenic fever in cancer patients suitable for early hospital discharge. *Supportive care in cancer: official journal of the Multinational Association of Supportive Care in Cancer* 16, 10 17-23 (2008).
15. Rubenstein, E. B. et al. Outpatient treatment of febrile episodes in low-risk neutropenic patients with cancer. *Cancer* 71, 3640-6 (1993).
16. Segal, B. H. et al. Prevention and treatment of cancer-related infections. *Journal of the National Comprehensive Cancer Network: JNCCN* 6, 122-74 (2008).
17. Jun, H. X. et al. Clinical guidelines for the management of cancer patients with neutropenia and unexplained fever. *International journal of antimicrobial agents* 26 Suppl 2, S 128-32; discussion S 133-40 (2005).
18. Hughes, W. T. et al. 2002 guidelines for the use of antimicrobial agents in neutropenic patients with cancer. *Clinical infectious diseases: an official publication of the Infectious Diseases Society of America* 34, 730-51 (2002).
19. Hendricks, A. M., Loggers, E. T. & Talcott, J. A. Costs of home versus inpatient treatment for fever and neutropenia: analysis of a multicenter randomized trial. *Journal of clinical oncology: official journal of the American Society of Clinical Oncology* 29, 3984-9 (2011).
20. Teuffel, O., Amir, E., Alibhai, S., Beyene, J. & Sung, L. Cost effectiveness of outpatient treatment for febrile neutropaenia in adult cancer patients. *British journal of cancer* 104, 1377-83(2011).
21. National Comprehensive Cancer Network (NCCN) Clinical Practice Guidelines in Oncology. Prevention and treatment of cancer-related infections. http://www.nccn.org (2011).
22. Levy, M. M. et al. 2001 SCCM/ESICM/ACCP/ATS/SIS International Sepsis Definitions Conference. *Critical care medicine* 31, 125 0-6 (2003).
23. Annane, D., Bellissant, F. & Cavaillon, J.-M. Septic shock. *Lancet* 365, 63-78
24. Freifeld, A., Sankaranarayanan, J., Ullrich, F. & Sun, J. Clinical practice patterns of managing low-risk adult febrile neutropenia during cancer chemotherapy in the USA. *Supportive care in cancer: official journal of the Multinational Association of Supportive Care in Cancer* 16, 18 1-91 (2008).
25. Innes, H., Billingham, L., Gaunt, C., Steven, N. & Marshall, E. Management of febrile neutropenia in the United Kingdom: time for a national trial? *British journal of cancer* 93, 1324-8 (2005).
26. Sung, L. et al. Inpatient versus outpatient management of low-risk pediatric febrile neutropenia: measuring parents' and healthcare professionals' preferences. *Journal of clinical oncology: official journal of the American Society of Clinical Oncology* 22, 3922-9 (2004).
27. Elting, L. S. et al. Outcomes and cost of outpatient or inpatient management of 712 patients with febrile neutropenia. *Journal of clinical oncology: official journal of the American Society of Clinical Oncology* 26, 606-11 (2008).
28. Escalante, C. P. et al. Outcomes of treatment pathways in outpatient treatment of low risk febrile neutropenic cancer patients. *Supportive care in cancer: official journal of the Multinational Association of Supportive Care in Cancer* 12, 657-62 (2004).

What is claimed is:

1. A system for out-patient, home monitoring and detection of chemotherapy induced febrile neutropenia in a patient, the system comprising:
a pulse oximeter for sensing photoplethysmographic signals of the patient;
a movement sensor for sensing movement of the patient and for correcting for motion and/or gravitational interferences in the patient's photolethysmographic signals resulting from said sensed movements;
a temperature sensor for sensing the patient's body temperature;
one or more point-of-care blood borne parameter sensors for sensing parameters in the patient's blood including neutrophil count;
a scale for measuring the patient's weight; and
a febrile neutropenia monitoring application, hosted at least partially on a server and electronically accessible over at least one network system to a patient computer,
wherein the febrile neutropenia monitoring application is configured to determine the patient's peripheral vascular resistance and heart rate based on information sensed by the pulse oximeter, and to receive information sensed by the pulse oximeter, the temperature sensor, the one or more blood borne parameter sensors and the scale and to determine, based on the received information, a change in the patient's condition, and should said change approach or be out of compliance with pre-determined criteria including a single body temperature reading of >38.3° C. or a temperature of >38° C. sustained for >1 hour with an absolute neutrophil count of <1000 cells/microL, indicative of the possible presence or deterioration of febrile neutropenia, provide an alarm upon a determination of the presence of or deterioration of febrile neutropenia in a patient.

2. The system of claim 1 further comprising a healthcare provider computer located remotely from the patient's home, wherein the febrile neutropenia monitoring application is configured to provide an alarm to the healthcare provider computer upon a determination of the presence or deterioration of febrile neutropenia in the patient.

3. The system of claim 2, wherein the febrile neutropenia monitoring application is configured to provide an alarm to the healthcare provider computer upon a determination of patient non-compliance with a patient monitoring protocol.

4. The system of claim 1 further comprising a blood pressure sensor,
wherein the febrile neutropenia monitoring application is configured to receive information sensed by the blood pressure sensor and to determine the presence or deterioration of febrile neutropenia based at least in part on the information sensed by the blood pressure sensor.

5. The system of claim 1, wherein the blood borne parameter sensors comprise a cell-based assay for sensing or counting monocytes.

6. The system of claim 1, wherein the febrile neutropenia monitoring application is configured to provide a communication to the patient computer, upon a determination of the presence or deterioration of febrile neutropenia in the patient, said communication prompting the patient to perform at least one of: seeking professional medical care, and begin taking antibiotics.

7. A method for out-patient home monitoring and detection of chemotherapy induced febrile neutropenia in a patient, the method comprising:
sensing photoplethysmographic signals of the patient including vascular resistance, heart rate and blood oxygen saturation with a pulse oximeter;
sensing movement of the patient and correcting for motion and/or gravitational interferences of the patient's photoplethysmographic signals resulting from said sensed movement;
sensing the patient's body temperature with a temperature sensor;
sensing the patient's weight with a scale;
sensing blood borne parameters in the patient's blood, including neutrophil count, with one or more point-of-care blood borne parameter sensors;
transmitting the sensed photoplethysmographic signals and blood borne parameters to a febrile neutropenia monitoring application;
determining, based on changes in the sensed photoplethysmographic signals and blood born parameters, if said signals are approaching or out of compliance with pre-determined criteria, including a single body temperature reading of >38.3° C. or a temperature of >38° C. sustained for >1 hour with an absolute neutrophil count of <1000 cells/microL, indicative of the presence or deterioration of febrile neutropenia; and
providing an alarm upon a determination of the presence of or deterioration of febrile neutropenia in a patient.

8. The method of claim 7 further comprising:
providing, by the febrile neutropenia monitoring application, an alarm to a healthcare provider computer located remotely from the patient's home upon a determination of the presence or deterioration of febrile neutropenia in the patient.

9. The method of claim 7 further comprising:
providing, by the febrile neutropenia monitoring application, an alarm to a healthcare provider computer upon a determination of patient non-compliance with a patient monitoring protocol.

10. The method of claim 7 further comprising:
sensing the patient's blood pressure, wherein the determining, by the febrile neutropenia monitoring application, is based on changes in the blood pressure information.

11. The method of claim 7, wherein the blood borne parameter sensors comprise a cell-based assay for sensing or counting at least one of neutrophils and monocytes.

12. The method of claim 7 further comprising:
providing, by the febrile neutropenia monitoring application, a communication to a patient computer, upon a determination of the presence or deterioration of febrile neutropenia in the patient, said communication prompting the patient to perform at least one of: seeking professional medical care and begin taking antibiotics.

13. A non-transitory computer readable medium containing instructions for home monitoring and detection of chemotherapy induced febrile neutropenia in a patient enabled at least in part on a processor of a computerized device, the instructions, which when executed by the processor, performing the steps of:
receiving photoplethysmographic signals of the patient including vascular resistance, heart rate and blood oxygen saturation from a pulse oximeter;
receiving correction signals for the photoplethysmographic signals based on sensed movement of the patient;
receiving patient body temperature signals from a temperature sensor;
receiving patient body weight signals from a scale;
receiving blood borne parameters including neutrophil count in the patient's blood from one or more point-of-care blood borne parameter sensors;
determining if said signals are approaching or out of compliance with pre-determined conditions, including a single body temperature reading of >38.3° C. or a temperature of >38° C. sustained for >1 hour with an absolute neutrophil count of <1000 cells/microL, indicative of the presence or deterioration of febrile neutropenia based on changes in the signals received from the photoplethysmographic sensor and the one or more blood borne parameter sensors; and
providing an alarm to a healthcare provider upon a determination of the presence or deterioration of febrile neutropenia in a patient.

* * * * *